United States Patent [19]

Ichinomiya et al.

[11] 4,417,587
[45] Nov. 29, 1983

[54] BLOOD PRESSURE MEASURING APPARATUS

[75] Inventors: Tsutomu Ichinomiya; Toshio Kusunoki; Tomohiro Kami, all of Hikone, Japan

[73] Assignee: Matsushita Electric Works, Ltd., Osaka, Japan

[21] Appl. No.: 294,620

[22] Filed: Aug. 20, 1981

[30] Foreign Application Priority Data

Aug. 25, 1980 [JP] Japan .................................. 55-116777

[51] Int. Cl.³ .............................................. A61D 5/02
[52] U.S. Cl. .................................................. 128/682
[58] Field of Search ................................ 128/680-683, 128/686

[56] References Cited

U.S. PATENT DOCUMENTS

| | | | |
|---|---|---|---|
| 3,308,811 | 3/1967 | Gillette et al. | 128/680 |
| 3,978,848 | 9/1976 | Yen et al. | 128/681 |
| 4,026,277 | 5/1977 | Toda et al. | 128/680 |
| 4,058,117 | 11/1977 | Kaspari et al. | 128/2.05 A |
| 4,252,127 | 2/1981 | Gemelke | 128/683 X |

FOREIGN PATENT DOCUMENTS

1259502  1/1968  Fed. Rep. of Germany ...... 128/680

*Primary Examiner*—Kyle L. Howell
*Assistant Examiner*—Francis J. Jaworski
*Attorney, Agent, or Firm*—Stevens, Davis, Miller & Mosher

[57] ABSTRACT

Apparatus is described for measuring both the systolic and diastolic blood pressure of an individual. A pressurable cuff having an additional tightening band for advantageously positioning a cuff and microphone on an artery is described. The microphone is connected to first the second filters having respective passbands for analyzing the frequency content for recovered pulse signals. The apparatus provides for automatic pressurizing and depressurizing of the cuff whereby the artery is occluded and opened to permit passage of the blood flow. The pressure at the time of receipt of signals from the filters is measured as the systolic pressure. The diastolic blood pressure is measured with apparatus in accordance with the invention by monitoring signals from one of the filters.

14 Claims, 11 Drawing Figures

BLOOD PRESSURE MEASURING APPARATUS

BACKGROUND OF THE INVENTION

The present invention relates to automatic blood pressure measuring devices. Specifically, an apparatus for automatically measuring and displaying values of systolic and diastolic blood pressure is described.

It is known to make measurements of blood pressure based upon the Korotkoff sound method. In the Korotkoff sound method, the artery of a patient in the upper arm area is pressurized by means of a pressurizable cuff wrapped around the upper arm. The pressurization rate applied to the upper arm area is in the vicinity of 20 mm hg/second and 30 mm hg/second. The pressure applied to the arm area is increased until it is 10 mm hg to 20 mm hg higher than the expected systolic or maximum blood pressure, at which point the arterial flow of blood is completely cut off. In this process, the cuff pressure is decreased gradually at a rate of 2 to 8 mm hg per second until the artery is able to pass a small amount of blood. During the systolic period of the heart beat, the arterial blood flow reaches a maximum speed and passes through the slightly opened artery. As blood flows towards the arterial wall, there is an attenuation vibration in the high frequency pulse wave produced by the blood which constitutes the aforesaid Korotkoff sound. At this time, cuff pressure approximates the systolic blood pressure. Further reduction of the pressure to the arm area produces pulse waves that are in synchronism with the Korotkoff sounds, and at the point where the artery is open and the heart is in the diastolic period, the Korotkoff sounds cease. The cuff pressure at this time expresses the diastolic blood pressure permitting a reading of both the systolic and diastolic blood pressure.

Prior art devices have depended upon detecting the Korotkoff sound pulse with a microphone. When the Korotkoff sound is above a specific output level, the cuff pressure is read to determine the systolic blood pressure. Corresponding to this measurement, the level of the Korotkoff sound signal is monitored to determine when it is below a predetermined level, at which time the cuff pressure is recorded at the diastolic blood pressure. The prior art improved upon detection of the Korotkoff sounds utilizing a first low-range filter, having a band pass between 30 and 50 hertz to extract the systolic Korotkoff sound signal low frequency components. Further, a second filter was employed which extracted the higher frequency components having a frequency between 80 to 120 hertz of the Korotkoff sound to measure the diastolic blood pressure. When the output from the low frequency filter ended, the pressure exerted by the cuff was recorded at the systolic blood pressure. When the output from the second filter ceased, the pressure applied by the cuff was recorded as the diastolic blood pressure.

Figure 5:
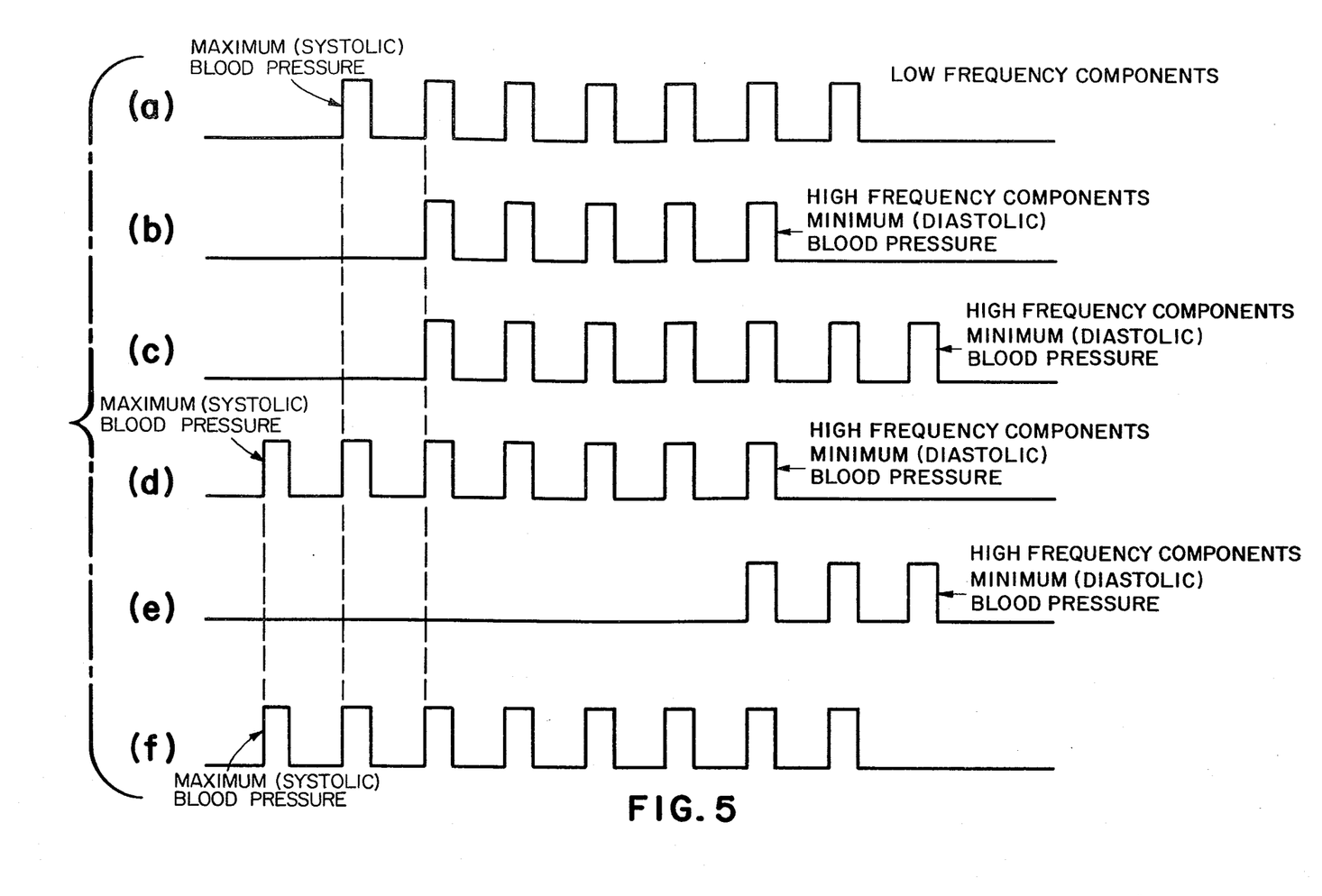
FIG. 5 illustrates the relationship between low frequency components of the Korotkoff sound signal and high frequency components with respect to the systolic and diastolic blood pressure of different patients.

This method provided for measurement errors due to the differences between the Korotkoff sounds produced by different patients. It occurs between patients that the relative appearance and time of disappearance of the low-range frequency components of the Korotkoff sound signal and the high-range frequency components differ from individual to individual. Referring to FIG. 5, the problems in using this technique are graphically illustrated. FIG. 5a shows the general pattern of the Korotkoff sound signal with respect to the low frequency components of the second signal. The high frequency components, as shown in FIG. 5b, occur somewhat later than the low frequency components and disappeared slightly before the low frequency components. Other individuals, however, have a pattern shown in FIG. 5c wherein the high frequency components disappear later than the low frequency components, and, in FIG. 5d, it is shown that there is still another signal pattern where the high frequency components appear before the low frequency components and therefore are not taken as an indication of the systolic blood pressure.

A further problem in using the prior art technique of blood pressure measurements is illustrated in FIG. 5e where the high frequency components appear slightly later than the low frequency components of the Korotkoff signal. Prior art devices are arranged to begin taking diastolic blood pressure measurements after the occurrence of 4 pulses from the first low frequency filter. The built in time delay presents problems with a pulse pattern of FIG. 5e. A pulse pattern of FIG. 5e would result in the diastolic blood pressure measuring technique having a starting point slightly later than the appearance of the high frequency components, avoiding measurement of the diastolic blood pressure altogether.

SUMMARY OF THE INVENTION

It is an object of the present invention to avoid errors in prior art blood pressure measuring techniques. It is the specific object of this invention to avoid measurement errors of the systolic and diastolic blood pressure resulting from variations between Korotkoff sounds from different patients. It is still a further object of the invention to permit a person to apply his own cuff to the arm without difficulty.

These and other objects are provided by an apparatus in accordance with the present invention. Apparatus is provided for measuring both the systolic and diastolic blood pressure of an individual. A pressurizable cuff is employed restricting the flow of blood through an artery in response to an applied pressure. A microphone located adjacent the artery provides signals to first and second filters. The first and second filters have respective pass bands for passing the lower frequency components of the emitted Korotkoff signals and the high frequency components thereof. The pressure provided by the cuff is increased to a predetermined maximum and, thereafter, decreased until a signal from either of said filters is detected. The pressure of the cuff at a time of receipt of this detection corresponds to the systolic pressure.

In one embodiment of the invention, the first detection of a systolic pressure initiates a re-pressurization of the cuff. The cuff pressure is then released and a second cuff pressure measurement is taken in response to a signal from the filters to determine a subsequent systolic pressure measurement. Apparatus is provided for comparing the first and subsequent systolic blood pressure measurements. When said measurements are within a predetermined range of each other, a recording device records the systolic pressure for the operator to visualize.

In the preferred embodiment of the apparatus, after two consecutive systolic pressure measurements are made and validated, the output of the second filter is monitored. At the conclusion of a signal produced by the second filter, the cuff is re-pressurized and de-pressurized while monitoring the output from the second filter which contains the high frequency components of the Korotkoff signal. The cuff pressure at the conclusion of a subsequently produced output signal from the second filter is compared with the previously measured cuff pressure. When the later cuff pressure is the same as the previously measured pressure, the subsequent pressure is recorded as the diastolic blood pressure. The preferred embodiment of the invention includes a cuff for restricting the flow of blood through an artery.

DESCRIPTION OF THE PREFERRED EMBODIMENT

Figure 1:
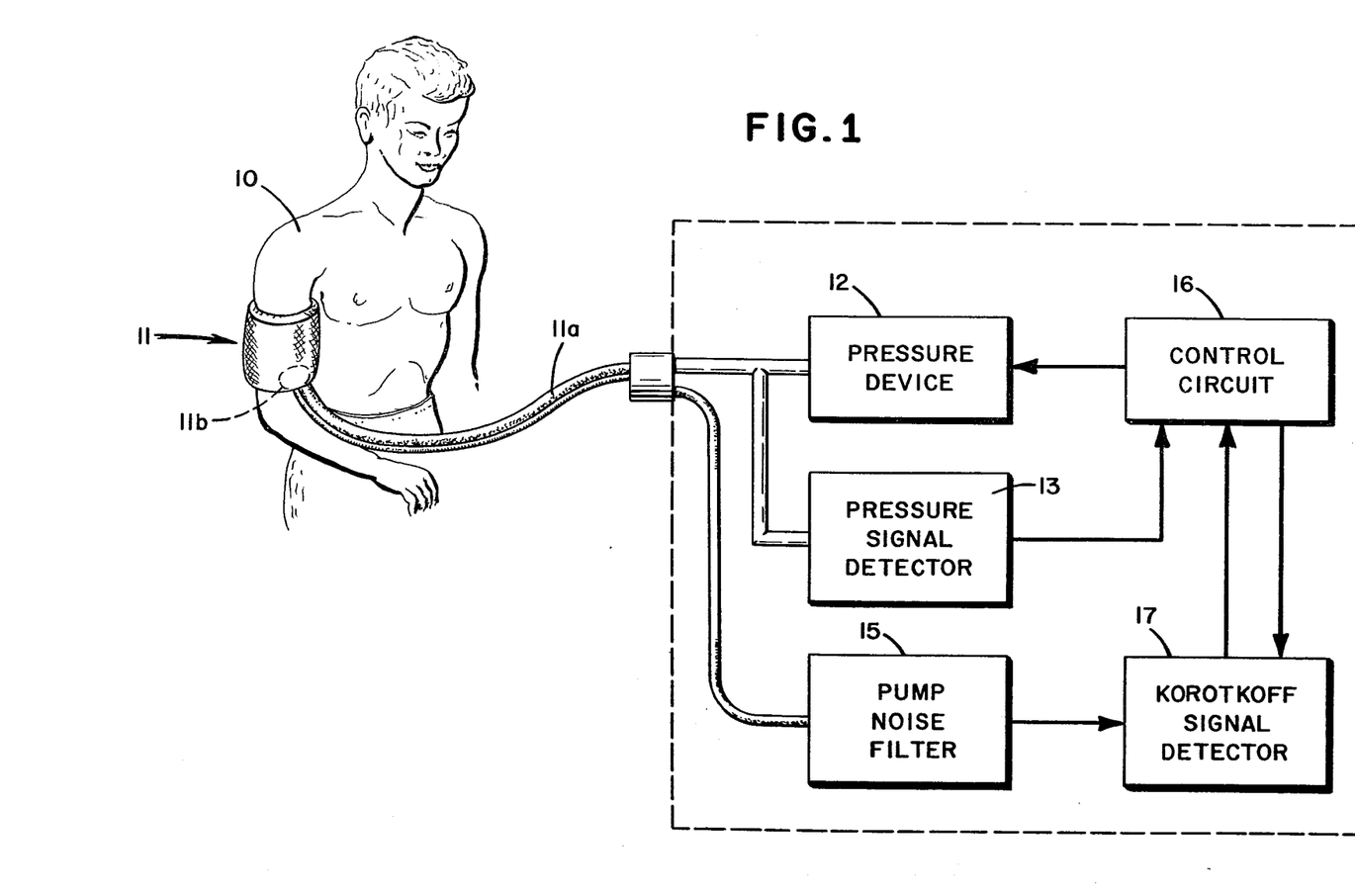
FIG. 1 is an overall block diagram of an embodiment of the present invention.

Referring now to FIG. 1, there is shown in block diagram form a blood pressure measuring device in accordance with one embodiment of the invention. The figure illustrates a patient 10 having a pressurizable occluding cuff 11 wrapped around one arm. The cuff 11 is pressurized through an air conduit 11a connected ultimately to a pressure device 12. Associated with the cuff 11 is a microphone 11b which is connected to a pump noise filter 15. A control circuit 16 in combination with pressure device 12 and pressure signal detector 13 provide for a cycling of the pressure applied by cuff 11 to the arm of the patient 10. A signal from control circuit 16 to pressure device 12 increases the pressure on the artery to a maximum level whereby the artery surrounded by the cuff 11 is occluded. This is determined by monitoring the Korotkoff sounds during pressurization. When the sounds cease, the pressure is increased to 20 mm hg above the point of cessation. Once this pressure is obtained, the pressure decreases at a substantially linear rate. During the decrease of the pressure, the artery opens to permit passage of the blood and the Korotkoff sounds occur. Microphone 11b detects signals due to the Korotkoff phenomena, and the result is applied to pump noise filter 15. Pump noise filter 15 is selected to remove substantially all noise which may emanate from the pressurizing device 12. The resulting filter signal is applied to a Korotkoff signal detector 17. The Korotkoff signal detector determines from the received sounds the systolic blood pressure. Once the systolic blood pressure is determined, the signal detector 17 determines the diastolic blood pressure in a manner to be explained with reference to FIG. 2.

Figure 4:
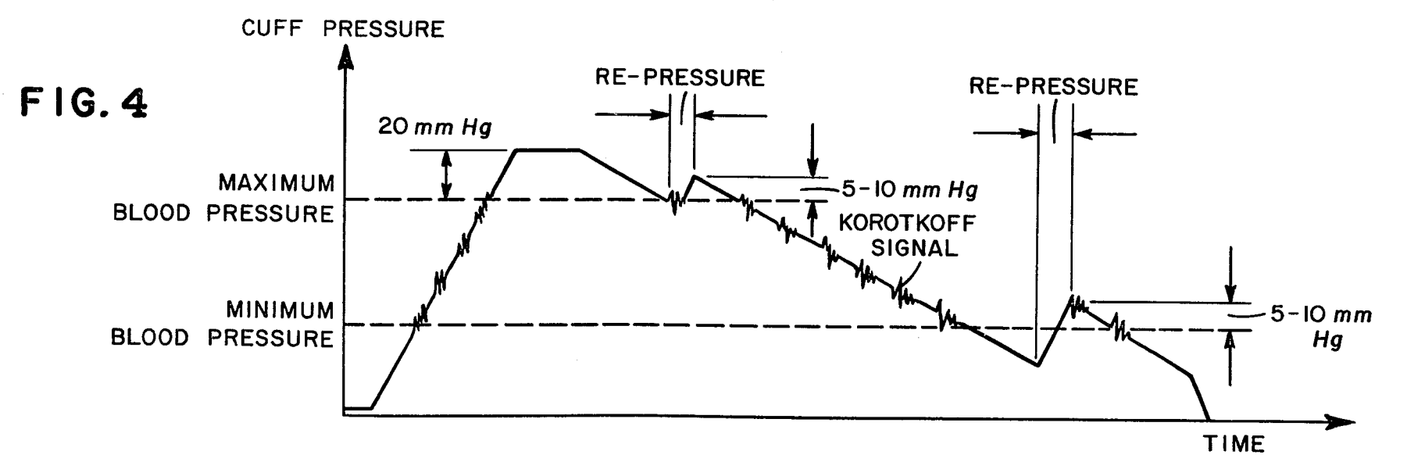
FIG. 4 demonstrates the relationship between cuff pressure and the reduction of Korotkoff signals produced by a pressurized artery.

Referring to FIG. 4, the operation of the apparatus of FIG. 1 is more completely described. The control circuit 16 may be a microprocessor controller that is programmed to provide a signal which, as shown in FIG. 4, linearly increases the pressure applied by pressure device 12 to the cuff 11. Control circuit 16 operates to initially pressurize cuff 11 to a pressure so that the artery, surrounded by cuff 11 is occluded. This is determined by monitoring the Korotkoff sounds during pressurization with Korotkoff detector 17. When the Korotkoff sounds cease, the pressure of cuff 11 is increased to a level 20 mm hg above the pressure corresponding to artery occlusion. Control circuit 16 thereafter produces a signal which decreases the pressure applied by pressure device 12. At the time the pressure is decreasing, the artery is opening and a first Korotkoff signal is produced. Korotkoff signal detector 17 indicates to control circuit 16 the time in which the first Korotkoff signal is received. At this time, control circuit 16, which may be a microprocessor having memory storage, stores a value of pressure which is present on the cuff 11 by sensing the output signal from pressure signal detector 13. Thus, an initial systolic blood pressure is determined when the first Korotkoff signal is produced.

Control circuit 16, upon detecting the first occurrence of a Korotkoff signal, re-pressurizes cuff 11 to a pressure 5–10 mm hg above the initial systolic blood pressure. The pressure is thereafter decreased by the control circuit 16 output signal until a second Korotkoff signal is received, and control circuit 16 wll once again determine the pressure applied on the cuff 11 by sensing the output signal from pressure signal detector 13. The control circuit 16 and Korotkoff signal detector 17 are arranged, as will be more fully described with respect to FIG. 2, to record a systolic blood pressure measurement corresponding to the subsequent systolic blood pressure measurement when the first and second measurements are within a predetermined range. In the event that the stored inital systolic blood measurement differs by more than a predetermined amount from the subsequent measured systolic blood pressure, control circuit 16 will initiate repressurization of the cuff 11 and subsequent Korotkoff signals will be detected and compared in the aforesaid sequence until two consecutive systolic blood pressures are determined to be within a predetermined comparison range. The most recently determined systolic blood pressure will then be recorded.

Figure 2:
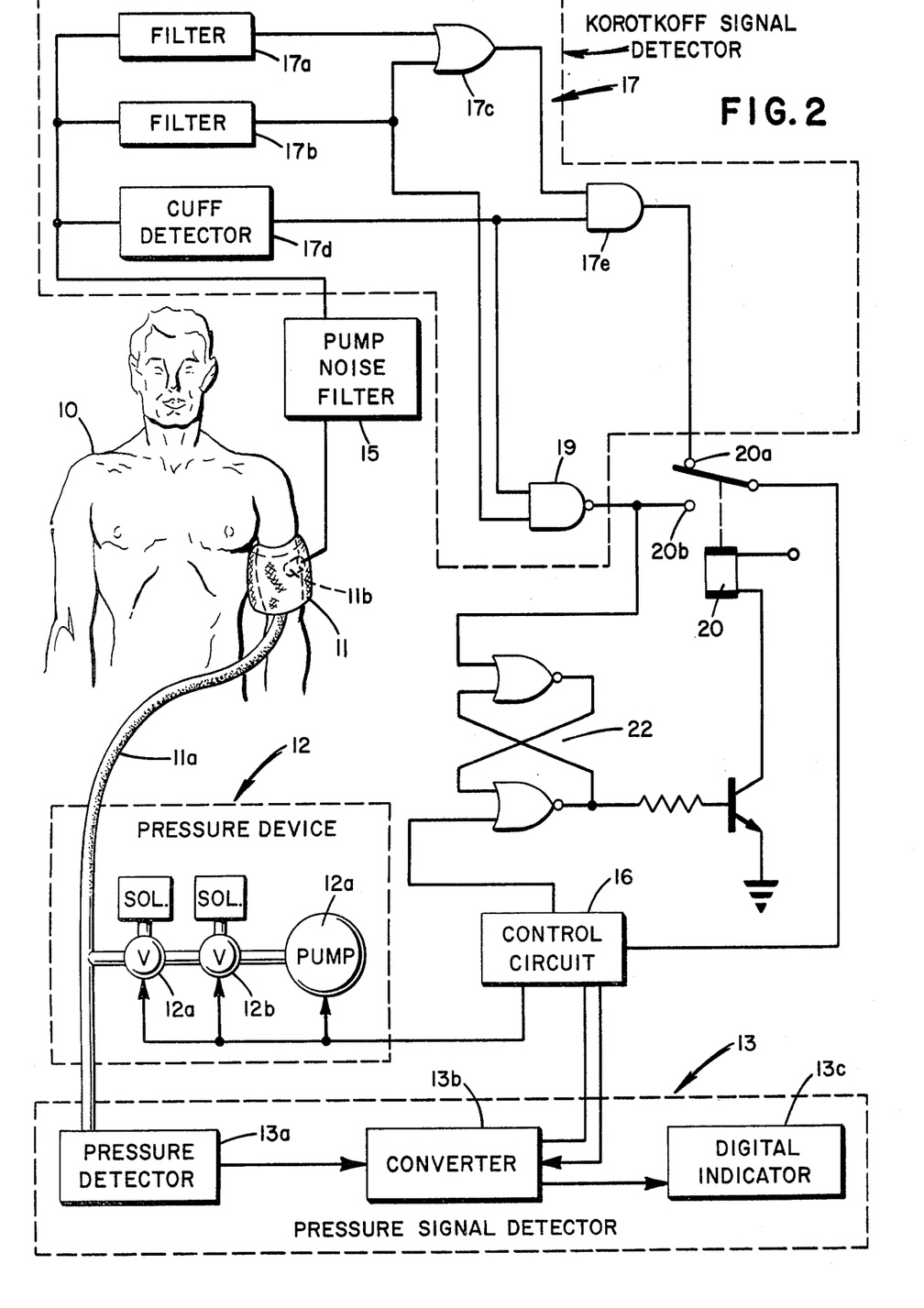
FIG. 2 is a more detailed illustration of an embodiment in accordance with the present invention

When two subsequent Korotkoff signals are detected which yield substantially the same systolic blood pressure measurements, control circuit 16 will enable that portion of Korotkoff signal detector 17 which measures the diastolic blood pressure. The apparatus of FIG. 1 will analyze successive Korotkoff sounds which occur after the systolic pressure is recorded. When the Korotkoff signal detector indicates that the artery is completely open and in the diastolic period, a cuff pressure is memorized. If 3–4 seconds elapse without receiving a successive sound pulse circuit 16 then causes pressure device 12 to repressurize cuff 11 5–10 mm hg above this level and the next Korotkoff sound is analyzed. The pressure on the cuff at the time that Korotkoff signal detector 17 produces an indication of a diastolic period is compared with the previous cuff pressure. When the two successively produced pressure readings are substantially the same, the diastolic pressure is determined to be the later of these pressures. Referring now to FIG. 2, there is shown a pump noise filter 15 which has an amplitude-frequency response for eliminating noise generated by rotation of the motor driving pressure pump 12a. It is contemplated that a motor rotational speed of less than 2,400 RPM or above 6,000 RPM is expected. In the case of a pump operating at less than 2,400 RPM, a filter is included to suppress noise having a frequency below 40 hertz. In the case of a motor operating at 6,000 RPM, pump noise in the vicinity of 100 hertz or greater is suppressed by pump noise filter 15. It is also of course possible to use a charging tank between the pump 12a and electromagnetic valve 12b to avoid the noise propagating from the pump motor to the cuff 11 thereby rendering unnecessary a pump noise filter 15.

Pressure device 12 comprises, in addition to pump 12a and solenoid valve 12b, a solenoid valve 12c operated to vent the pressure from cuff 11. The pressure device 12 is of conventional design, operating from a control signal from control circuit 16 opening and closing solenoid valve 12b and 12c to provide a pressure which increases and decreases in accordance with FIG. 4.

The Korotkoff signal detector 17 comprises first and second filters 17a and 17b. Filter 17a removes the low frequency components of an audio signal from microphone 11a representing the Korotkoff signal. Filter 17b provides the high frequency components of the produced microphone signal representing the Korotkoff signal. First filter 17a has a bandpass amplitude frequency response between 30 and 50 hz. Second filter 17b has a bandpass amplitude frequency response between 80 and 120 hz. An OR gate 17c combines the outputs of the filters.

The combined outputs of the filters produced by OR gate 17c represent the occurrence of a Korotkoff signal. The OR gate 17c therefore provide a signal for indicating when the pressure applied by cuff 11 should be memorized by control circuit 16.

Figures 3A, 3B:
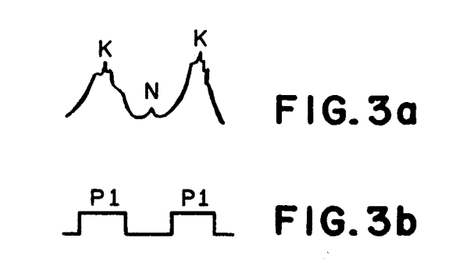
FIG. 3a illustrates a detected Korotkoff sound signal with noise.
FIG. 3b illustrates the pulse noise P1 resulting from detection of a Korotkoff sound signal.
Figure 3C:
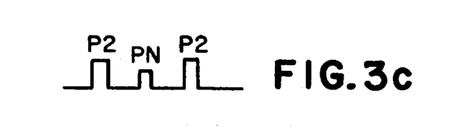
FIG. 3c shows the Korotkoff sound pulse P2 with a noise pulse (N) produced from a noise signal.

A further improvement of this invention is the use of a noise suppressing detector 17d for suppressing noise which may occur between Korotkoff signals from falsely triggering a blood pressure reading. Referring to FIG. 3a, two Korotkoff signals are shown with a noise pulse occurring therebetween. The pulses represented by FIG. 3b are pulses which represent the Korotkoff signals. In FIG. 3c, there is shown a noise signal which accompanies the pressure pulses P2 produced from the microphone 11a. In the event that OR gate 17c produces a noise pulse PN, then AND gate 17e will not be enabled, as the signals P1 from cuff detector 17d as shown in FIG. 3b will not contain a synchronous pulse corresponding to the noise pulse. One way of implementing the cuff noise detector 17d is to have a threshold detector employed which will eliminated pulses having a marginal amplitude, these pulses representing noise pulses.

The production of a true indication of a Korotkoff signal by AND gate 17e is applied to normally closed relay contact 20a.

At the initial energizing of the control circuit 16 by the operator, the signals from AND gate 17e are applied to control circuit 16. Control circuit 16 is, in the case of a microprocessor, programmed to provide, a signal which will decrease and increase the pressure in accordance with FIG. 4. As was indicated with respect to the description of FIG. 4, when OR gate 17e indicates receipt of an initial Korotkoff signal, control circuit 16 provides a signal for re-pressurizing cuff 11 to approximately 5–10 mm hg above the level which initiated a first Korotkoff signal. Simultaneously, control circuit 16 memorizes the value of pressure indicated by pressure detector 13. The output from pressure detector 13 is converted into a digital number of converter 13b. Converter 13b, continuously connected to pressure detector 13a, is enabled by a signal from control circuit 16 at the time that the initial Korotkoff signal is detected by OR gate 17e. Where a microprocessor is used as part of control circuit 16, this digital number is directly received and stored for comparison with a second measured systolic blood pressure.

The initial determination of the systolic blood pressure is stored in a memoory circuit of control circuit 16 and repressurization of the cuff 11 occurs. Control circuit 16 supplies a signal for venting the pressure from cuff 11 and a subsequent Korotkoff signal is produced by OR gate 17e. At this time, the two quantities, first and second received digitalized Korotkoff signals from converter 13b are compared by the microprocessor in a known manner. When the result of this comparison indicates that the first and second Korotkoff signals differ by less than a predetermined amount, control circuit 16 enables converter 13b to provide a signal to digital indicator 13c which may be a permanently recording type indicator for recording the subsequent systolic blood pressure measurement.

At the conclusion of the successful production of two Korotkoff signals from AND gate 17e, which represent systolic blood pressure levels which are substantially the same, control circuit 16 will activate reset input (R) of flip-flop 22. The armature of relay 20 is moved to normally open contact 20b. Thus, AND gate 19 is connected to control circuit 16.

AND gate 19 combines the output of the filter 17b representing the high frequency components of the sound pulse and the output of noise detector 17d. Thus, noise pulses which are not passed by the noise detector 17b do not provide a false indication that a Korotkoff signal has been produced.

Once the output of AND gate 19 is connected to control circuit 16, the high frequency filter 17B is monitored. The next succeeding Korotkoff sound pulse produces an output from filter 17B indicating the diastolic period of the heart. The pressure on the cuff 11 is memorized at this time. The concluding portion of the signal from filter 17b signifies the time for taking the pressure measurement. If three to four seconds elapse after receipt of this indication, without receiving a successive Korotkoff sound pulse, control circuit 16 will provide a signal for pressure device 12 for re-pressurizing cuff 11 5–10 mm hg above the level producing the last received Korotkoff sound pulse. The pressure thence decreases as shown in FIG. 4 until filter 17B provides a second indication of a Korotkoff sound. Once the second indication is received the pressure level producing the second indication is compared with the pressure level producing the first indication of a diastolic heart period. When these quantities are within a predetermined range, the last pressure level is recorded as the diastolic blood pressure. In the event the comparison is not obtained, the cycle is reproduced re-pressurizing the cuff and monitoring the output of filter 17B until two successive Korotkoff signals have been found yielding substantially the same diastolic blood pressure measurement.

At the time the correct diastolic blood pressure measurement has been determined, converter 13B is enabled by a signal from control circuit 16 to provide a converted pressure measurement for display or recording by digital indicator 13C. At the same time, flip-flop 22 is restored to permit further systolic blood pressure measurements, and the armature of relay 20 returns to monitor the AND gate 17 output signal.

Figure 6:
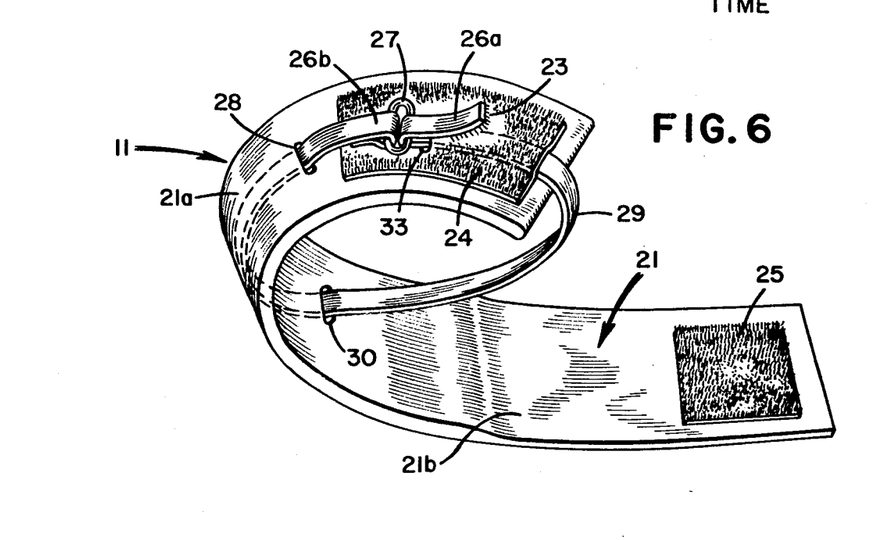
FIG. 6 is an overall view of a cuff suitable for pressurizing an artery.
Figure 7:
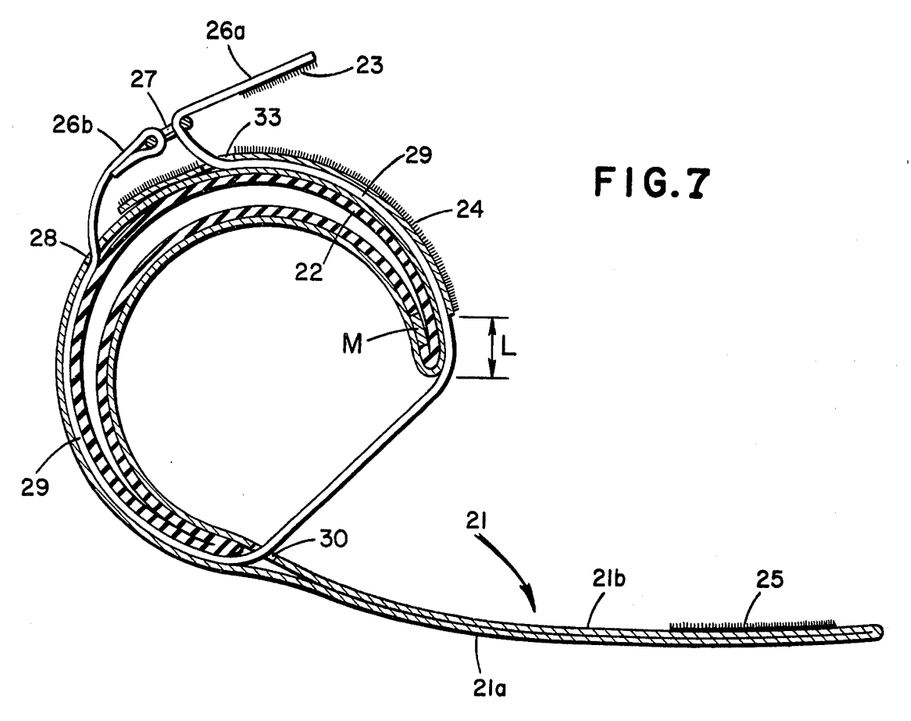
FIG. 7 is an additional view of the cuff of FIG. 6 showing the bladder.

A cuff used with the above described blood pressure measuring apparatus is shown in FIGS. 6 and 7. The cuff shown in these figures facilitates the use of the blood pressure measuring apparatus by permitting an individual patient to attach the cuff to his arm with the remaining free hand permitting the measurement to be taken in a convenient manner.

Referring now to FIGS. 6 and 7, there is shown a cuff band 21 comprising first and second layers, 21b and 21a of material. Between the layers 21a and 21b is inserted an inflatable bladder 22. The inflatable bladder 22 is pressurized via an opening in the bladder 22 from a source of high pressure air. The bladder 22 is depressurized by releasing the positive pressure applied to the opening in the bladder. The bladder 22 is shaped along an arc which exceeds 180°. The bladder is made of a semi-rigid material to hold the arcuate shape shown in the figures.

A tightening band 29 is provided along the exterior of the bladder surface. The tightening band 29 has one end 26b terminating in a ring member 27. The band extends from the terminated end 26b through a hole 28 in second layer 21a around the exterior of the bladder towards the remaining end of the cuff band 21. The tightening band 29 extends through a hole 30 in first layer 21b adjacent the ends of the arcuate bladder 22. The tightening band 29 thence continues towards the remaining end of the arcuate bladder 22, around the exterior surface of both the bladder 22 and second layer 21a. The tightening band is threaded through ring 27 and is terminated with a fastening means 23.

Figure 8:
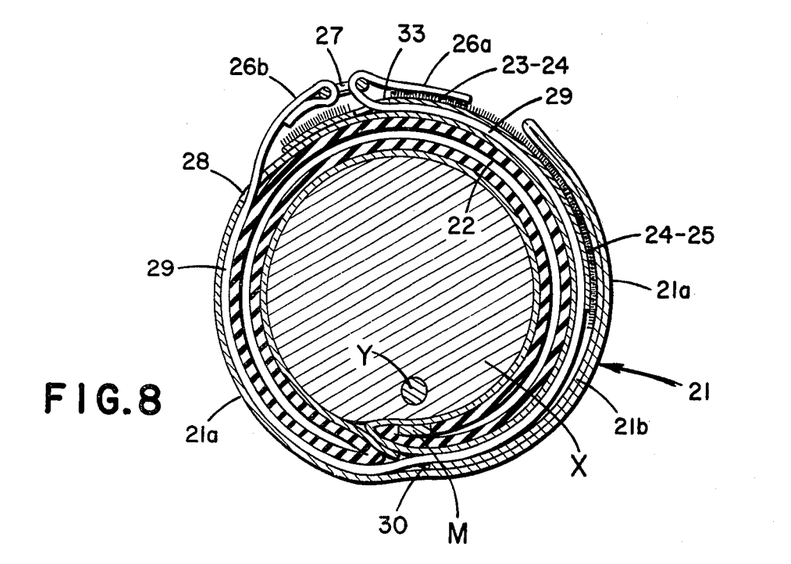
FIG. 8 illustrates the implementation of the cuff of FIGS. 6 and 7 in a blood pressure meaasuring mode.

Referring now to FIG. 8, there is shown the cuff 21 enclosing the arm X of a patient. The cuff is applied with the free hand to the arm by inserting the arm between the tightening band 29 and the interior surface of the bladder 22. The microphone M is inserted adjacent the bladder 22 wall. The tightening band 29 is pulled at the free end 26a until the cuff is rigidly secured for pressurization. The second end 26a of the tightening band wrapped around the arm in a continuous direction has fastener 23 placed into engagement with fastener 24 located on layer 21a. The second end of tightening band 26a having fastener 23 exits the opening 33. When the tightening band 29 is taut, the free end 26a is connected with fastener 23 to fastener 24.

Thus, the patient's arm is equipped with the pressurizable cuff by merely using his free hand. The free hand places the cuff around the arm, tightening the tightening band. It is preferable to make the tightening band 29 of an elastic material. This permits the final fitting of the cuff to be achieved with relative ease before fastening the remaining end of tightening band 29. This is accomplished by wrapping the remaining end bearing fastener 25 around tightening band 29 for engagement with fastener 24.

The cuff of FIGS. 6, 7 and 8 normally has an outer circumference of 220 millimeters for which the arm is capable of being enclosed. A distance L is left between the fastener material 23 and the edge of the arcuate bladder. Thus, by selecting distance L to be an appropriate length, the circumference of most individual's arm X may be accommodated by selecting distance L so that the cuff will occlude the artery of the smallest patient.

Figure 9:
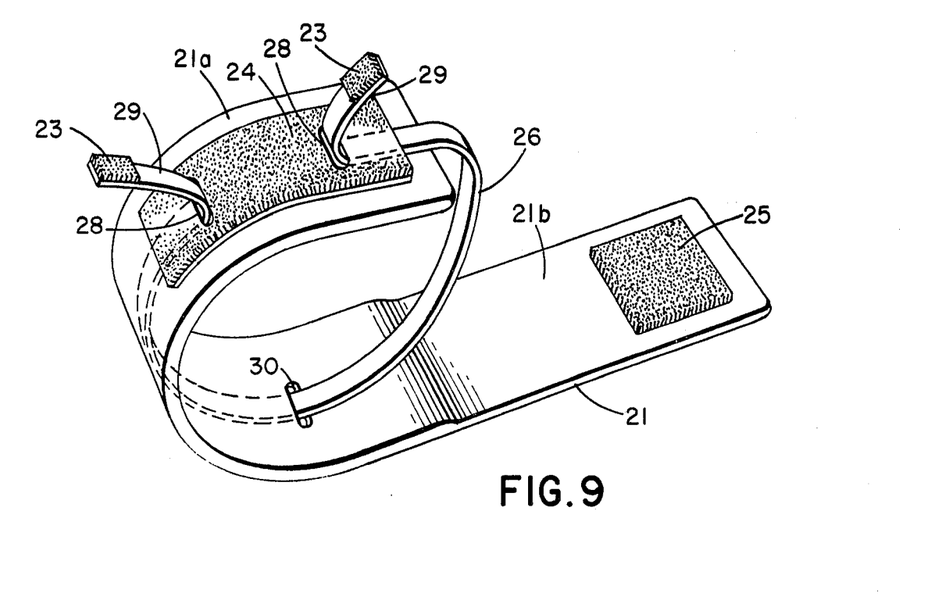
FIG. 9 is an additional embodiment of a cuff suitable for use in blood pressure measuring devices according to the present invention.

Referring now to FIG. 9, an additional embodiment of a cuff used with the blood pressure measuring apparatus of the invention is shown. The fasteners terminating the ends of supplementary band 29 each contain a fastener 23 for holding the ends of the tightening bands in position. Each end of the band 26a and 26b is equipped with a releasable fastener 23.

Figure 10:
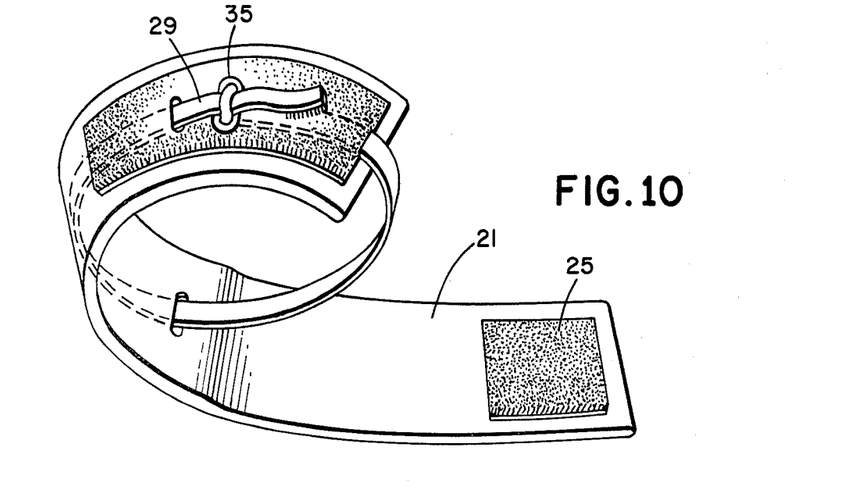
FIGS. 10 and 11 illustrate yet another embodiment of a cuff suitable for making blood pressure measurements.
Figure 11:
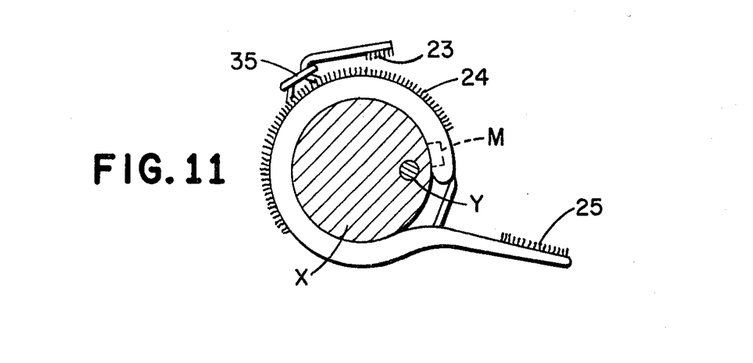

A further embodiment of the cuff used with the elastronic automatic blood pressure apparatus of the invention is shown in FIG. 10. The tightening band outer surface is affixed to a sewn on fastener 35. The sewn fastener is connected to the fastener material 24. Additional fastening material 24 is put on the free end of tightening band 29 whereby it may be readily fixed in place. FIG. 11 shows that the microphone may be advantageously positioned to sense the emitted signals without interference from the ring 27 or other components used to secure the tightening band.

Thus there has been described with respect to one embodiment a automatic blood pressure measuring apparatus. Those skilled in the art will recognize other embodiments described more particularly by the claims which follow.

What is claimed is:

1. An automatic blood pressure measuring apparatus comprising:
   a pressurizable cuff for restricting the flow of blood through an artery;
   a microphone adapted to be attached to said cuff for detecting sound emanating from said artery;
   a pump means connected to said cuff to cyclically pressurize and depressurize said cuff in response to an electrical signal;
   a circuit connected to receive a signal from said microphone comprising:
   a first filter for passing low frequency signals in the sounds detected by said microphone;
   a second filter for passing high frequency signals in the sounds detected by said microphone;
   means for combining output signals from said filters to provide a first detection signal;
   relay means having a normally closed contact and a normally open contact selectively connected to a movable contact in response to a control signal, said normally closed contact receiving a signal from said means for combining indicating that high or low frequency signals have been received;
   means for recording the pressure of said cuff in response to an enabling signal;
   a control circuit connected to said pump means including a signal analyzing means connected to said movable contact, said signal analyzing means comparing the pressure of said cuff at a time each of successive signals are received from said means for combining, said control circuit providing a signal to said pump means for cyclically pressurizing said cuff between an initial maximum pressure and a minimum pressure, said cuff pressure decreasing from said maximum pressure until said means for combining produces an output signal whereby said cuff is re-pressurized to a pressure level intermediate said maximum pressure and a pressure which produced said means for combining output signal, said pressure thence decreasing to said minimum level so that additional signals are produced, said control circuit switching and movable arm into contact with said open contact when two successive pressures occurring at the time successive signals are produced by said means for combining are determined to be less than a predetermined amount and simultaneously supplying an enabling signal to said means for recording whereby a systolic blood pressure is recorded; said control circuit further including means for storing the pressure of said cuff when said second filter supplies a first signal after said movable arm is connected to said open contact, said control means thereafter repressurizing said cuff to a pressure intermediate said diastolic blood pressure and said maximum blood pressure, thence decreasing said cuff pressure until a second signal is received from said second filter, said control circuit comparing the pressure of said cuff at the time said second signal is received, said control circuit providing an enabling signal to said means for recording when said stored cuff pressure is substantially equivalent to the pressure of said cuff at the time said second signal is received.

2. The apparatus of claim 1, further comprising: means for filtering said microphone signal to eliminate pump noise contained in said signal.

3. The apparatus of claim 1, further comprising: a cuff noise detector for eliminating noise pulses which are non-synchronous with said high or low frequency signals.

4. The apparatus of claim 1, wherein: said control circuit provides a signal to said pump means for establishing an initial maximum pressure during measurement of said systolic pressure, said signal thence decreasing said pressure until a first signal is produced, thence increasing said pressure to pressure 5-10 mm hg above the pressure producing said first signal, thence decreasing said pressure until a second signal is produced.

5. The apparatus of claim 1, further comprising means for inhibiting recording of said diastolic pressure until two successively measured diastolic pressure levels are substantially the same.

6. The apparatus of claim 1 further comprising means for inhibiting the repressurization of said cuff after said second filter supplies a first signal if a subsequent signal is received within 3 to 4 seconds later.

7. An automatic blood pressure measuring apparatus comprising:
a cuff for restricting the flow of blood through an artery in response to an applied pressure;
a microphone, adapted for attachment to said cuff, for detecting sound emanating from said artery and producing signals;
first and second filters connected to receive signals from said microphone, said first filter having a passband for passing lower frequency components of said signals, said second filter having a passband for higher frequency components of said signals;
means for detecting low and high frequency signals from said first and second filters, respectively;
means for pressurizing and depressurizing said cuff;
a pressure detector to measure the pressure of said cuff;
means for storing the value of the pressure of said cuff, measured by said pressure detector, during depressurization of said cuff, either when a high or low frequency signal is first detected by said means for detecting or when said means for detecting detects a high frequency signal, which is followed by at least a 3-4 second period where no successive high frequency signal is detected;
means to compare pressures consecutively-stored by said means for storing;
means to initially activate said means for pressurizing and depressurizing said cuff, whereby the pressure of said cuff is increased by a preset amount above the pressure of said cuff existing when signals from said first or second filters cease to be received by said means for detecting and then the pressure of said cuff is decreased such that when a signal from said first or second filter is first detected by said means for detecting, a pressure corresponding to an initial systolic pressure is measured by said pressure detector and stored by said means for storing;
means to reactive said means for pressurizing and depressurizing after said means for detecting receives the signal from said first or second filter corresponding to said initial systolic pressure, whereby the pressure of said cuff is increased by a predetermined amount above said initial systolic pressure and then the pressure of said cuff is decreased such that when another signal from said first or second filter is first detected by said means for detecting, a pressure corresponding to a subsequent systolic pressure is measured by said pressure detector and stored by said means for storing;
means for activating said means for comparing to determine a first difference corresponding to the difference between said subsequent pressure and said initial systolic pressure; and
means for repeatedly reactivating said means for pressurizing and depressurizing and said means for comparing to increase the pressure of said cuff by said predetermined amount above the subsequent systolic pressure last stored by said means for storing and then decrease the pressure of said cuff, whereby additional subsequent systolic pressures are measured by said pressure detector and stored by said means for storing if said first difference exceeds a present value and until the difference between consecutively-stored subsequent systolic pressure is less than said preset value.

8. The apparatus of claim 7 wherein the pressurized cuff for occluding an artery in a human limb comprises:
a pressurized bladder, said bladder formed of a semi-rigid material along an arc for partially enclosing said limb, said bladder having an interior surface which upon inflation restricts the flow of blood in an artery carried by said limb;
a double-layered cuff band, said cuff band enclosing said bladder, whereby first and second layers are adjacent said interior surface of said bladder and an exterior surface of said bladder, respectively said double-layered cuff band extending at one end a distance away from said bladder terminating in a first fastener on an exterior surface of said second layer;
a supplementary tightening band having first and second ends, said first end fastenable to said cuff band, said band extending through a hole in an exterior layer of said cuff band around said bladder towards said remaining end of cuff band, thence extending through a hole in an interior layer of said cuff band around the remaining exterior surface of said bladder exterior of said band, said tightening band, terminating in a second fastener; and a third fastener on the exterior surface of said first layer adjacent said cuff band one end for receiving said second fastener when said band is pulled through said ring tightening said bladder against said limb, and for receiving said first fastener when said remaining end of said cuff is wrapped around said limb.

9. The apparatus of claim 7 wherein the pressurized cuff for occluding an artery in a human limb comprises:

a pressurized bladder, said bladder formed of a semi-rigid material along an arc for partially enclosing said limb, said bladder having an interior surface which upon inflation restricts the flow of blood in an artery carried by said limb;

a double-layered cuff band, said cuff band enclosing said bladder, whereby first and second layers are adjacent said interior surface of said bladder and an exterior surface of said bladder, respectively said double-layered cuff band extending at one end a distance away from said bladder terminating in a first fastener on an exterior surface of said second layer;

a supplementary tightening band having first and second ends, said first end terminating in a ring, said band extending through a hole in an exterior layer of said cuff band around said bladder towards said remaining end of cuff band, thence extending through a hole in an interior layer of said cuff band around the remaining exterior surface of said bladder exterior of said band, said tightening band, terminating in a second fastener; and a third fastener on the exterior surface of said first layer adjacent said cuff band one end for receiving said second fastener when said band is pulled through said ring tightening said bladder against said limb, and for receiving said first fastener when said cuff band is wrapped around said arm.

10. The apparatus of claim 7 further comprising:

means to continue decreasing the pressure of said cuff when said first difference or said difference between said consecutively-stored subsequent systolic pressures differ by less than said preset value;

means to reactivate said means for pressurizing and depressurizing when a period of at least 3–4 seconds has elapsed between detection of successive high frequency signals by said means for detecting and after an initial diastolic pressure is measured by said pressure detector and stored by said means for storing when said means for detecting detects a high frequency signal which is followed by a 3–4 second period where no successive high frequency signal is detected, whereby the pressure of said cuff is increased by a fixed amount above said initial diastolic pressure and then the pressure of said cuff is decreased such that when said means for detecting detects a high frequency signal, which is followed by at least 3–4 second period where no successive high frequency signal is detected, a subsequent diastolic pressure is measured by said pressure detector and stored by said means for storing;

means to activate said means for comparing to determine a second difference corresponding to the difference between said initial and subsequent diastolic pressures; and means for repeatedly reactivating said means for pressurizing and depressurizing and said means for comparing to increase the pressure of said cuff by said fixed amount above the subsequent diastolic pressure last stored by said means for storing and then decrease the pressure of said cuff, whereby additional subsequent diastolic pressures are measured by said pressure detector and stored by said means for storing if said second difference exceeds a predetermined value and until consecutively stored subsequent diastolic pressures are less than said predetermined value.

11. The apparatus of claim 7, further comprising;

means for recording the systolic pressure last stored by said means for storing when said first difference or said difference between said consecutively-stored subsequent systolic pressures differ by less than said preset value.

12. The apparatus of claim 11, wherein said means for recording is activated only if said first difference or said difference between consecutively-stored subsequent systolic pressures is substantially zero.

13. The apparatus of claim 7, wherein said means to reactivate said means for pressurizing and depressurizing is designed so that the predetermined amount is 5–10 mm hg.

14. The apparatus of claim 10, wherein said means to reactivate said means for pressurizing and depressurizing is designed so that the fixed amount is 5–10 mm hg.

* * * * *